US010064731B2

(12) United States Patent
Moser et al.

(10) Patent No.: US 10,064,731 B2
(45) Date of Patent: *Sep. 4, 2018

(54) BLADE-LIKE SHAFT OF A HIP JOINT PROSTHESIS (71) Applicant: Smith and Nephew Orthopaedics AG, Rotkreuz (CH)

(72) Inventors: Walter Moser, Kaufdorf (CH); Alex Seidl, Zurich (CH); Dirk Wunderle, Zurich (CH)

(73) Assignee: Smith & Nephew Orthopaedics AG, Rotkreuz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,502

(22) Filed: Nov. 21, 2016

(65) Prior Publication Data

US 2017/0065421 A1    Mar. 9, 2017

Related U.S. Application Data (63) Continuation of application No. 12/067,635, filed as application No. PCT/EP2006/007842 on Aug. 8, 2006, now Pat. No. 9,498,340.

(30) Foreign Application Priority Data

Sep. 20, 2005  (DE) .................. 10 2005 044 872
Oct. 12, 2005  (DE) .................. 10 2005 048 873

(51) Int. Cl.
    A61F 2/32      (2006.01)
    A61F 2/46      (2006.01)
    (Continued)

(52) U.S. Cl.
    CPC .............. *A61F 2/3662* (2013.01); *A61F 2/36* (2013.01); *A61F 2/367* (2013.01); *A61F 2/3676* (2013.01);
    (Continued)

(58) Field of Classification Search
    CPC ........ A61F 2/36; A61F 2/3607; A61F 2/3609; A61F 2/3662–2/3676
    See application file for complete search history.

(56) References Cited

U.S. PATENT DOCUMENTS 4,279,042 A    7/1981  Andriacchi et al.
4,310,931 A    1/1982  Muller
(Continued)

FOREIGN PATENT DOCUMENTS

EP    0032165 A2    7/1981
EP    0145939 A2    6/1985
FR    2678510 A     1/1993

OTHER PUBLICATIONS

International Search Report; European Patent Office; International Application No. PCT/EP2006/007842; dated Nov. 7, 2006, 4 pages.
(Continued)

Primary Examiner — Marcia Watkins
(74) Attorney, Agent, or Firm — Taft Stettinius & Hollister LLP (57) ABSTRACT A blade-like stem of a hip joint prosthesis for anchoring in the femur, including a prosthesis neck portion and a femur-anchoring portion extending therefrom and having a proximal end and a distal end, the femur-anchoring portion including a proximal arcuate portion extending from a location adjacent the proximal end and having a radius of curvature that changes in a distal-to-proximal direction, and the femur-anchoring portion further including a distal tapered portion extending from the proximal arcuate portion toward the distal end.

18 Claims, 5 Drawing Sheets (51) Int. Cl.
*A61F 2/36* (2006.01)
*A61F 2/30* (2006.01)

(52) U.S. Cl.
CPC ............... *A61F 2002/30148* (2013.01); *A61F 2002/30151* (2013.01); *A61F 2002/30153* (2013.01); *A61F 2002/30158* (2013.01); *A61F 2002/30205* (2013.01); *A61F 2002/30253* (2013.01); *A61F 2002/30255* (2013.01); *A61F 2002/30257* (2013.01); *A61F 2002/30332* (2013.01); *A61F 2002/30606* (2013.01); *A61F 2002/30616* (2013.01); *A61F 2002/30785* (2013.01); *A61F 2002/30795* (2013.01); *A61F 2002/365* (2013.01); *A61F 2002/368* (2013.01); *A61F 2002/3625* (2013.01); *A61F 2002/3686* (2013.01); *A61F 2002/4631* (2013.01); *A61F 2002/4635* (2013.01); *A61F 2220/0033* (2013.01); *A61F 2230/008* (2013.01); *A61F 2230/0017* (2013.01); *A61F 2230/0019* (2013.01); *A61F 2230/0026* (2013.01); *A61F 2230/0067* (2013.01); *A61F 2230/0076* (2013.01); *A61F 2230/0078* (2013.01)

(56) References Cited

U.S. PATENT DOCUMENTS

| | | | |
|---|---|---|---|
| 4,404,693 A | 9/1983 | Zweymuller | |
| 4,753,657 A | 6/1988 | Lee et al. | |
| 4,908,035 A * | 3/1990 | Deckner | A61F 2/367 |
| | | | 623/23.15 |
| 5,156,627 A * | 10/1992 | Amstutz | A61F 2/30767 |
| | | | 623/22.41 |
| 5,888,210 A | 3/1999 | Draenert | |
| 6,168,632 B1 | 1/2001 | Moser et al. | |
| 6,383,228 B1 * | 5/2002 | Schmotzer | A61F 2/3662 |
| | | | 623/23.15 |
| 6,540,788 B1 | 4/2003 | Zweymuller | |
| 6,613,094 B2 | 9/2003 | Zweymuller | |
| 6,808,539 B2 | 10/2004 | Zweymuller | |
| 7,004,973 B2 | 2/2006 | Zweymuller | |
| 7,175,668 B2 | 2/2007 | Zweymuller | |
| 7,497,875 B1 | 3/2009 | Zweymuller | |
| 7,749,278 B2 | 7/2010 | Frederick et al. | |
| 8,337,565 B2 * | 12/2012 | Wunderle | A61B 17/1659 |
| | | | 623/22.11 |
| 9,498,340 B2 * | 11/2016 | Moser | A61F 2/36 |
| 2005/0055103 A1 | 3/2005 | Badatcheff et al. | |
| 2005/0267586 A1 | 12/2005 | Sidebotham | |
| 2006/0206212 A1 | 9/2006 | Zweymuller | |
| 2006/0276904 A1 | 12/2006 | Zweymuller | |

OTHER PUBLICATIONS

Written Opinion of the International Searching Authority; European Patent Office; International Application No. PCT/EP2006/007842; dated Mar. 20, 2008; 9 pages.

Canadian Office Action; Canadian Intellectual Property Office; Canadian Patent Application No. 2,622,010; dated Oct. 17, 2012; 2 pages.

English Translation of Notification of Reasons for Rejection regarding counterpart Japanese Patent Application No. 2008-530349; Japanese Patent Office; dated May 25, 2011.

\* cited by examiner

BLADE-LIKE SHAFT OF A HIP JOINT PROSTHESIS

CROSS-REFERENCE TO RELATED APPLICATIONS

The present application is a continuation of U.S. patent application Ser. No. 12/067,635 filed Oct. 15, 2008 and issued as U.S. Pat. No. 9,498,340 on Nov. 22, 2016, which is a U.S. National Phase of International PCT Application No. PCT/EP2006/007842 filed Aug. 8, 2006, which claims priority to German Patent Application No. 10 2005 044 872.0 filed Sep. 20, 2005 and German Patent Application No. 10 2005 048 873.0 filed Oct. 12, 2005, the contents of each application incorporated herein by reference in its entirety.

FIELD OF THE INVENTION

The invention relates to a blade-like stem of a hip joint prosthesis for anchoring in the femur, having a portion comprising a prosthesis neck and a femur-anchoring portion tapering towards a distal end.

BACKGROUND

Figure 6:
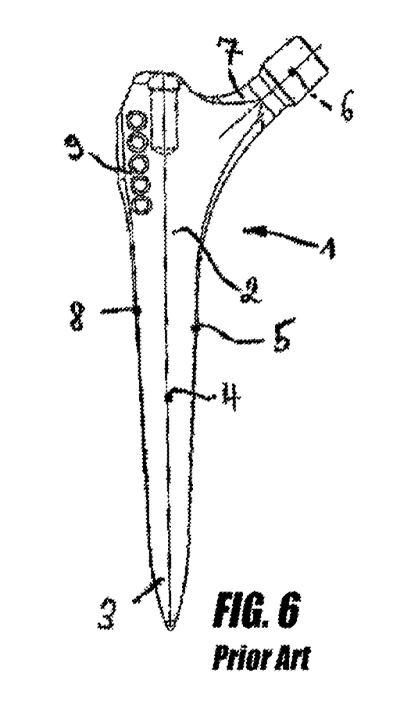
FIG. 6 depicts a prior art hip joint prosthesis.

A blade-like stem generally known in the art is described in EP 0 240 815 B1. A stem corresponding generally to FIG. 6 is shown and described therein. Accordingly, that stem 1 comprises a portion comprising a prosthesis neck 7 on the one hand and a femur-anchoring portion 2 tapering towards a distal end 3 on the other hand. That femur-anchoring portion widens conically all round from the distal end 3 in the direction of the stem longitudinal axis 4. The medial narrow side 5 merges out of the cone into a continuously curved arc which ends in a plane which, running perpendicular to the prosthesis neck axis 6, terminates the prosthesis neck 7 towards the stem blade, i.e. the femur-anchoring portion 2. The prosthesis neck 7 ends in an outwardly conically tapering pin on which a spherical joint head (not shown) can be placed.

The lateral narrow side 8 widens out of the conical widened portion to form a trochanter wing 9 before merging, via a shoulder of the stem blade or anchoring portion, into the prosthesis neck termination plane.

In both cases, a stem-receiving space, that is to say a corresponding cavity, has to be provided beforehand in the femur, that being effected by means of a shaping instrument, especially a rasp, corresponding to the shape of the stem. Such shaping instruments or rasps correspond exactly to the geometry of the stem in question or differ specifically therefrom in order to obtain a predetermined undersize for a press-fit or a predetermined oversize as space for a cement mantle.

Once the hip joint has been opened and the neck of the femur resectioned, in the proximal femur the bony bearing is prepared for receiving the anchoring stem. According to the shape of the stem, the bony anchoring bed is created using a suitable shaping instrument, especially a rasp, by movement down along the stem axis. For moving down into the medullary space, which is filled with spongy bone and soft tissue, the rasp is driven forwards by means of a weight acting as a hammer or using some other suitable instrument. In the case of a curved stem axis, the shaping instrument or rasp is moved down in an arc along a curved path, while in the case of a straight stem axis the rasp is driven forward along a straight line corresponding substantially to the axis of the proximal medullary space.

Figure 4:
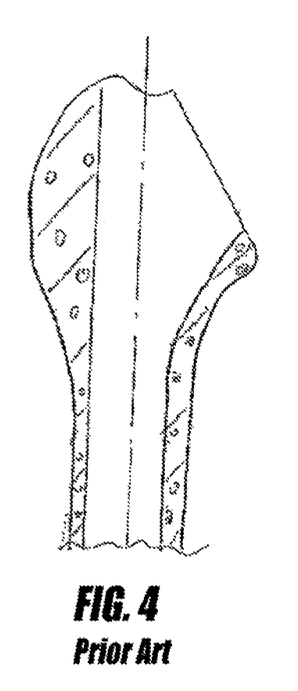
FIG. 4 depicts a resected bone for insertion of a straight stem prosthesis.

For cementless anchoring of hip stems, the configuration of the anchoring portion as a straight stem has proved especially suitable clinically. This concept allows a secure implantation technique, high primary stability and good ingrowth behavior. The current surgical techniques for such stems generally require the medullary space to be opened not only in the plane of the resection surface of the neck of the femur, but also further laterally into the region of the greater trochanter. Reference is made in this respect to FIG. 4. That Figure shows that a resection of portions of the tendon insertions in that region is also generally necessary. The extent of that resection of course depends upon the individual shape of the proximal femur and upon the shaping of the straight stem, among other things.

More recently, there has been an increase in implantations of joint endoprostheses carried out using minimally invasive surgical techniques. The aim of such techniques is more rapid rehabilitation of the patient, which is associated with a reduction in pain and a shorter stay in hospital. Minimally invasive surgical techniques keep operative trauma, especially in respect of the functionally significant structures, to a very low level. For the functioning of the hip joint the important structural features are the muscles and tendons. The aim of minimally invasive implantation techniques is inter alia to avoid resections and detachments of tendon and muscle insertions in the region of the greater trochanter. Classic straight stems accordingly have disadvantages for the use of minimally invasive techniques.

To avoid resections in the region of the tendon insertions on the greater trochanter, in the case of straight stems the lateral area can be chamfered in the region of the trochanter. Straight stems having a flattened shoulder have been proposed. An example is the so-called Muller straight stem shown and described in "Technique d'implantation de protheses totales de Muller par voie laterale transgluteale", Encyclopedie Medico-Chirurgicale (Paris) 44666, 1991.

Figure 5:
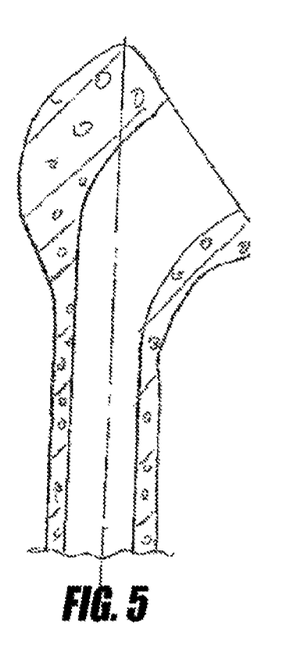
FIG. 5 depicts a resected bone with an undercut for insertion of a prosthesis.

The aim of that flattened shoulder is to avoid major defects in the region of the ridge of the trochanter. When shaping that flattened portion, a proportion of the lateral stem area, which proportion is constant within the size system, was generally configured with straight shaping inclined relative to the stem axis or with a radius. The rasp corresponding to the implant was generally made geometrically identical to the implant. From the technical standpoint, the rasp is used to create an undercut in the region of the greater trochanter, as can be seen in FIG. 5.

In the case of implantation of a hip stem, the bony bed is shaped using rasps of increasing size up to the size giving the best fit, the rasp in question following the shape of the existing bed formed by the preceding rasp size. Because the distal portion of the straight stem is affected by moving down along a straight axis, compromises are made in terms of exact fit in respect of the inclined or curved shoulder area. That is influenced, however, by the surgeon's rasp technique and individual bone quality.

SUMMARY

The present invention, described below, comprises a stem typically used for cementless anchoring in the femur. In principle, however, the present invention described below is intended to also relate, for example, to cemented stems as well as other stems.

Improving upon the above-mentioned prior art, one aim of the present invention is to provide a blade-like stem of the kind mentioned at the beginning that is especially suitable for minimally invasive surgical techniques. In so doing, the advantages of conventional straight stem implants should generally be retained, but muscle and tendon insertions should be protected as much as possible.

That problem is solved according to one embodiment of the invention as follows: the lateral narrow side of the stem comprises a distal straight portion and a proximal arcuate portion, the straight portion extending over a length of from 60% to 75% of the total length of the stem.

DETAILED DESCRIPTION

Figure 1:
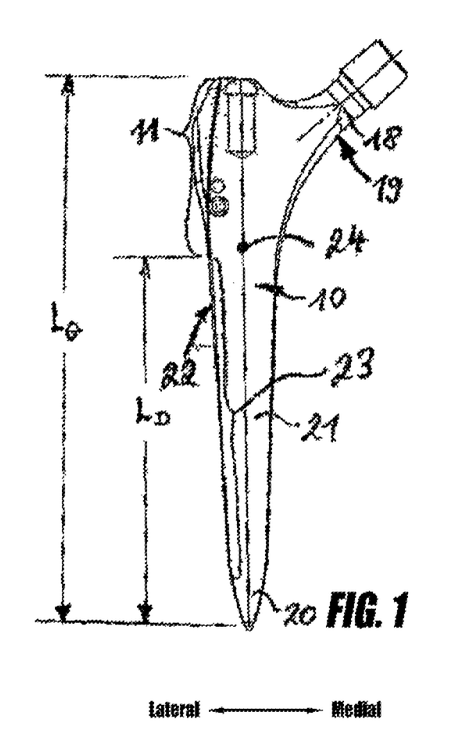
FIG. 1 depicts a schematic side view of one embodiment of a hip joint prosthesis.
Figure 2:
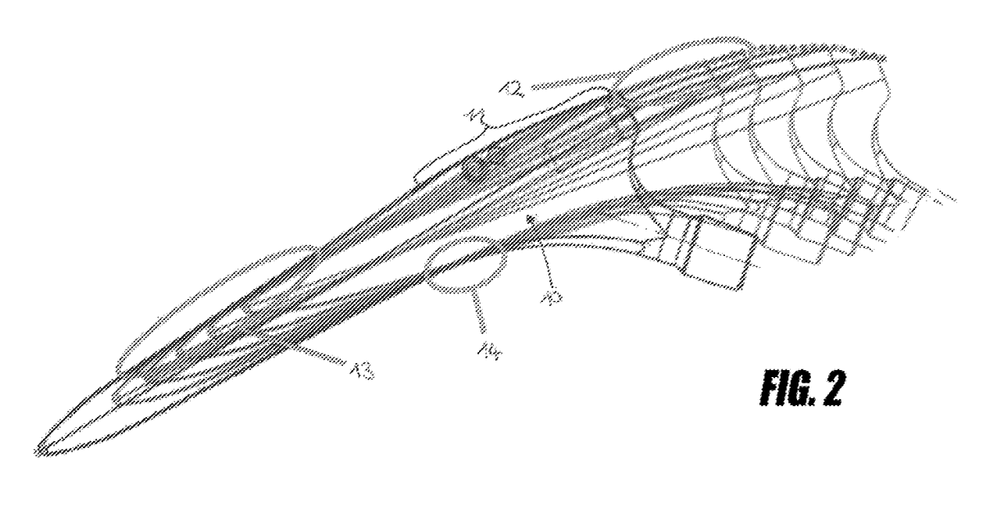
FIG. 2 depicts the path of the hip joint prosthesis upon entering a cavity.

A preferred shape of the convex proximal arcuate portion of a shaft stem comprises an arcuate portion that can be in the form of a "tractrix," which is described or defined by the proximal end of the lateral narrow side of the stem on introduction thereof (or of a corresponding rasp) into a complementary cavity in the femur while the contact between the lateral-distal and proximal-medial stem contour on the one hand and the associated boundary of the cavity on the other hand is maintained. The preferred shape of the proximal-lateral shoulder area is therefore derived from the guidance of the stem in the bony bed, as shown in FIG. 2. The lateral-proximal stem curvature 11 of the stem 10 corresponds to the curve 12 which is described by the proximal end of the lateral narrow side of the stem 10 on introduction thereof into a complementary cavity in the femur, on condition that the contact between the lateral-distal stem contour 13 and the proximal-medial stem contour 14 on the one hand and the associated boundary of the cavity (not shown herein) on the other hand is retained. A stem 10 constructed in accordance with one embodiment of the invention is otherwise shown in side view (ventral or dorsal) in FIG. 1, and moreover in comparison with a conventional blade-like stem according to FIG. 6 or EP 0 240 815 B1. FIG. 1 shows some differences from the prior art. The lateral side of the trochanter wing 9 according to FIG. 6 has been trimmed in FIG. 1 as a result of the lateral-proximal arcuate portion 11 with the advantage that there is correspondingly less interference with the ridge of the trochanter and, in particular, muscle and tendon insertions are also less severely affected during implantation or formation of the cavity for the stem 10. The contact zones in the region of the so-called Shenton's arch (region 14 in FIG. 2) and at the lateral-distal end (region 13 in FIG. 2) describe an arc along the lateral shoulder. That arc is described by a polynomial (curve of the xth order). That curve can follow on continuously from the lateral-distal stem geometry; preferably, however, it forms an angle therewith. In any case, the lateral-proximal arcuate portion is so configured that over the entire introduction path of the distal straight stem portion the shoulder has contact with or generally constant spacing from the bone structure in the trochanter region. There is thus achieved an optimum, exactly fitting shoulder area with respect to the bony bed with gap-free seating or with a predetermined gap for cement, according to whether a cementless or cemented implantation is to be carried out.

Figure 3:
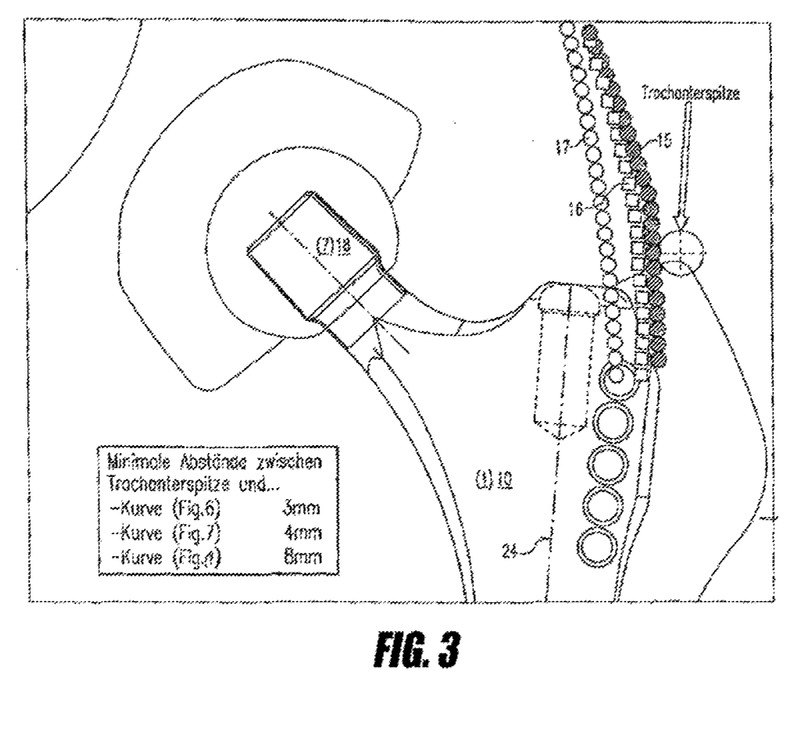
FIG. 3 depicts introduction paths of a proximal end of various hip joint prostheses.
Figure 7:
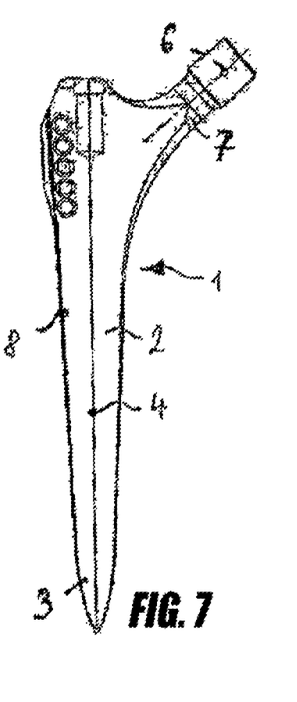
FIG. 7 depicts a schematic side view of another embodiment of a hip joint prosthesis.

In principle, it would also be possible to continue the lateral-distal straight portion in the proximal region in accordance with FIG. 7. That embodiment, however, is very much less protective of muscle and tendons than the embodiment according to the invention in accordance with FIG. 1. That can be seen very clearly especially from FIG. 3, which shows the introduction paths of the proximal end of the lateral narrow side of the stem for the versions in accordance with FIG. 6, FIG. 7 and FIG. 1. The introduction path 15 applies to the construction in accordance with FIG. 6 (prior art). The introduction path 16 applies to the construction according to FIG. 7 and the introduction path 17 applies to the configuration according to the invention in accordance with FIG. 1. Accordingly, there is least interference with the trochanter in the case of the embodiment according to the invention.

Also with reference to FIG. 1, it should be pointed out that the Figure shows a blade-like stem 10 of a hip joint prosthesis for anchoring in the femur, the stem being constructed in accordance with an embodiment of the invention. The stem has a portion 19 comprising a prosthesis neck 18 on the one hand and a femur-anchoring portion 21 tapering towards a distal end 20 on the other hand, the lateral narrow side 22 of which comprises a distal straight portion 23 and a proximal arcuate portion 11, the straight portion 23 extending over a length $L_D$ of from 60% to 75% of the total length $L_G$ of the stem 10. In the embodiment shown, the lateral straight portion 23 can merge continuously into the lateral arcuate portion 11, that is to say it is tangential. As already mentioned, however, it is entirely acceptable and in accordance with the invention for that transition to comprise a discontinuity, and/or be obtuse-angled.

As already mentioned above, it is especially advantageous for the lateral arcuate portion 11 to be in the form of a kind of "tractrix" which is described or defined by the proximal end of the lateral narrow side of the stem 10 on introduction thereof into a complementary cavity in the femur while the contact between the lateral-distal and proximal-medial stem contour on the one hand and the associated boundary of the cavity on the other hand is maintained. In this respect reference is again made to FIG. 2.

Depending upon the size of the stem and the external conditions, the proximal arcuate portion 11 is preferably configured with a constant, however especially continuously or discontinuously changing radius of between 200 mm and 500 mm.

It has also proved practical for the proximal arcuate portion 11 to be configured with a radius that becomes increasingly larger continuously or discontinuously from distal to proximal.

The arcuate portion 11 can especially also be in the form of a hyperbolic, parabolic or elliptical portion such that towards the distal end of the arcuate portion the portion in question merges into the conical straight portion 23 at a predetermined point at which the tangent forms with the stem axis 24 an angle equal to half the cone angle.

In connection with the stem itself, it should also be mentioned that the anchoring portion widens conically over the length of the lateral-distal straight portion 23 starting from the distal end 20 in the direction of its longitudinal axis 24 either all round or only laterally-medially.

It should also be mentioned that the cross-section of the stem 10 is preferably rectangular, but may also be trapezoidal or rhombic.

The mentioned all-round conical widening of the anchoring portion 21 has a cone angle of about from 0.5° to 6°, especially about from 1° to 3°. In some embodiments, the anchoring portion 21 can widen on only the ventral and/or dorsal side.

Figure 8A:
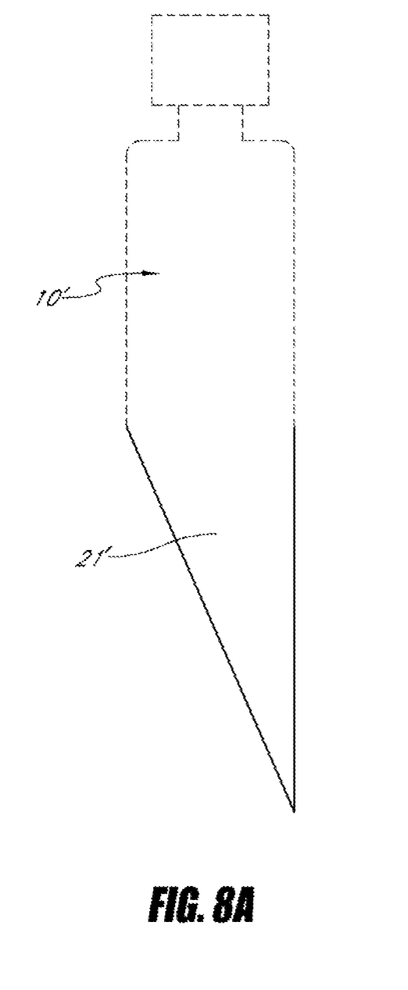
FIG. 8A depicts a schematic front view of another embodiment of a hip joint prosthesis.
Figure 8B:
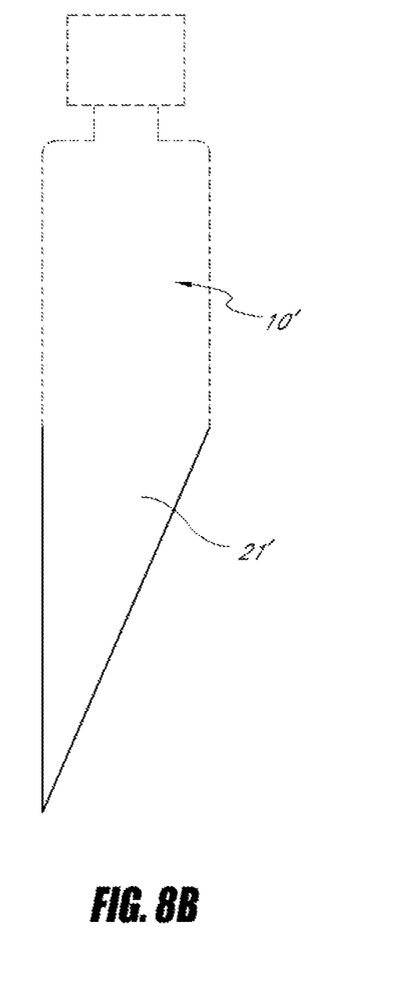
FIG. 8B depicts a schematic front view of another embodiment of a hip joint prosthesis.

FIGS. 8A and 8B depict other non-limiting embodiments, where an anchoring portion 21' of a prosthesis stem 10' widens on the ventral or dorsal sides. FIG. 8A depicts this widening on the ventral side. FIG. 8B depicts this widening on the dorsal side.

All the features disclosed in the application documents are claimed as being important to the invention, insofar as they are novel over the prior art individually or in combination.

REFERENCE NUMERALS

Prior Art 1 stem
2 femur-anchoring portion
3 distal end
4 longitudinal axis
5 medial narrow side
6 prosthesis neck axis
7 prosthesis neck
8 lateral narrow side
9 trochanter wing Invention 10 stem
11 proximal-lateral stem curvature (lateral-proximal arcuate portion)
12 curve
13 lateral-distal stem contour
14 proximal-medial stem contour
15 introduction curve for stem according to FIG. 6
16 introduction curve for stem according to FIG. 7
17 introduction curve for stem according to FIG. 1
18 prosthesis neck
19 portion
20 distal end
21 femur-anchoring portion
22 lateral narrow side
23 distal-lateral straight portion
24 stem axis

What is claimed is:

1. A hip joint prosthesis stem for anchoring in a femur, comprising:
   a prosthesis neck portion; and
   a femur-anchoring portion extending from the prosthesis neck portion and having a proximal end and a distal end, and including:
      a proximal arcuate portion extending from a location adjacent the proximal end and along a tractrix curvature; and
      a distal tapered portion extending from the proximal arcuate portion toward the distal end.

2. The hip joint prosthesis stem of claim 1, wherein the tractrix curvature decreases in a distal-to-proximal direction.

3. The hip joint prosthesis stem of claim 1, wherein the distal tapered portion merges tangentially into the proximal arcuate portion.

4. The hip joint prosthesis stem of claim 1, wherein the femur-anchoring portion has a total length extending from the proximal end to the distal end;
   wherein the proximal arcuate portion extends over a length of the femur-anchoring portion of from 25% to 40% of the total length; and
   wherein distal tapered portion extends over a length of from 60% to 75% of the total length.

5. A hip joint prosthesis stem for anchoring in a femur, comprising:
   a prosthesis neck portion; and
   a femur-anchoring portion extending from the prosthesis neck portion and having a proximal end and a distal end, and including:
      a proximal arcuate portion extending from a location adjacent the proximal end along a tractrix curvature and having a radius of curvature that changes in a distal-to-proximal direction; and
      a distal tapered portion extending from the proximal arcuate portion toward the distal end.

6. The hip joint prosthesis stem of claim 5, wherein the radius of curvature of the proximal arcuate portion becomes increasingly smaller in the distal-to-proximal direction.

7. The hip joint prosthesis stem of claim 5, wherein the radius of curvature of the proximal arcuate portion continuously changes in the distal-to-proximal direction.

8. The hip joint prosthesis stem of claim 7, wherein the radius of curvature of the proximal arcuate portion continuously decreases in the distal-to-proximal direction.

9. The hip joint prosthesis stem of claim 5, wherein the radius of curvature changes between 200 mm and 500 mm.

10. The hip joint prosthesis stem of claim 5, wherein the femur-anchoring portion has a total length extending from the proximal end to the distal end; and
    wherein the proximal arcuate portion extends over a length of the femur-anchoring portion of from 25% to 40% of the total length; and
    wherein the distal tapered portion extends from a location adjacent the distal end and over a length of from 60% to 75% of the total length.

11. The hip joint prosthesis stem of claim 5, wherein the distal tapered portion merges into the proximal arcuate portion at an obtuse angle.

12. The hip joint prosthesis stem of claim 5, wherein the distal tapered portion defines a taper angle between 0.5° to 6°.

13. The hip joint prosthesis stem of claim 5, wherein the distal tapered portion widens in a lateral-medial direction from the distal end toward the proximal arcuate portion.

14. The hip joint prosthesis stem of claim 5, wherein the distal tapered portion merges tangentially into the proximal arcuate portion.

15. A hip joint prosthesis stem for anchoring in a femur, comprising:
    a prosthesis neck portion; and
    a femur-anchoring portion extending from the prosthesis neck portion and having a proximal end and a distal end, and including:
       a proximal arcuate portion extending from a location adjacent the proximal end along a tractrix curvature and having a radius of curvature that decreases in a distal-to-proximal direction; and a distal tapered portion extending tangentially from the proximal arcuate portion toward the distal end.

16. The hip joint prosthesis stem of claim 15, wherein the radius of curvature of the proximal arcuate portion continuously decreases in the distal-to-proximal direction.

17. The hip joint prosthesis stem of claim 15, wherein the femur-anchoring portion has a total length extending from the proximal end to the distal end;
   wherein the proximal arcuate portion extends over a length of the femur-anchoring portion of from 25% to 40% of the total length; and
   wherein distal tapered portion extends over a length of from 60% to 75% of the total length.

18. The hip joint prosthesis stem of claim 15, wherein the radius of curvature changes between 200 mm and 500 mm.

* * * * *